(12) United States Patent
Franiak-Pietryga et al.

(10) Patent No.: US 9,877,985 B2
(45) Date of Patent: Jan. 30, 2018

(54) APPLICATION OF MALTOTRIOSE-COATED 4TH GENERATION POLYPROPYLENEIMINE DENDRIMER PPI-G4-OS-MAL-III

(71) Applicant: UNIWERSYTET LÓDZKI, Lódź (PL)

(72) Inventors: Ida Franiak-Pietryga, Lódź (PL); Maria Bryszewska, Lódź (PL); Dietmar Appelhans, Dresden (DE); Barbara Klajnert-Maculewicz, Lódź (PL)

(73) Assignee: UNIWERSYTET LODZKI, Lodz (PL)

( * ) Notice: Subject to any disclaimer, the term of this patent is extended or adjusted under 35 U.S.C. 154(b) by 0 days.

(21) Appl. No.: 14/650,521

(22) PCT Filed: Dec. 6, 2013

(86) PCT No.: PCT/PL2013/000163
§ 371 (c)(1),
(2) Date: Jun. 8, 2015

(87) PCT Pub. No.: WO2014/088435
PCT Pub. Date: Jun. 12, 2014

(65) Prior Publication Data
US 2015/0306134 A1    Oct. 29, 2015

(30) Foreign Application Priority Data
Dec. 6, 2012  (PL) .................................... P 401936

(51) Int. Cl.
*A61K 31/785*   (2006.01)
*A61K 9/50*    (2006.01)
*C08G 83/00*    (2006.01)
*A61K 47/48*    (2006.01)

(52) U.S. Cl.
CPC .......... *A61K 31/785* (2013.01); *A61K 9/5015* (2013.01); *A61K 47/48192* (2013.01); *C08G 83/004* (2013.01)

(58) Field of Classification Search
CPC ... A61K 31/785; A61K 9/5015; C08G 83/004
See application file for complete search history.

(56) References Cited

U.S. PATENT DOCUMENTS

2009/0208580 A1   8/2009   Shi et al.

FOREIGN PATENT DOCUMENTS

WO    WO 2009/156446    12/2009

OTHER PUBLICATIONS

Barbara Ziemba et al: "Influence of fourth generation poly(propyleneimine) dendrimers on blood cells", Journal of Biomedical Materials Research Part A, vol. 100A, No. 11, Nov. 24, 2012 (Nov. 24, 2012), pp. 2870-2880, XP055107843, ISSN: 1549-3296, DOI: 100.1002/jbm.a.34222 abstract; figure 1; table I.

(Continued)

*Primary Examiner* — Trevor Love
(74) *Attorney, Agent, or Firm* — Horst M. Kasper, Esq.

(57) ABSTRACT

The application of maltotriose-coated 4th generation polypropyleneimine dendrimer PPI-G4-OS-Mal-III containing 25-45% of peripheral amines groups coated with maltotriose particles to make a drug for treating neoplastic proliferation diseases, particularly chronic lymphocytic leukemia.

5 Claims, 3 Drawing Sheets

Pattern of PPI-G4-OS-Mal-III dendrimer particle (56) References Cited

OTHER PUBLICATIONS

Barbara Ziemba et al: "Genotoxicity poly(propylene imine) dendrimers", BIOPOLYMERS, vol. 97, No. 8, Aug. 17, 2012 (Aug. 17, 2012), pp.642-648, XP055107840, ISSN: 0006-3525, DOI: 10.1002/bip.22056 abstract; figure 1; table I.

Aleksandra Szulc et al: "Characteristics of complexes between poly(propylene imine) dendrimers and nucleotides", New Journal of Chemistry, vol. 36, No. 8, Jan. 1, 2012 (Jan. 1, 2012), p. 1610, XP055107855, ISSN: 1144-0546, DOI: 10.1039/c2nj40165g abstract; figure 3.

Franiak-Pietryga-IDA; Ziolkowska Ewelina; Ziemba Barbara; Appelhans Dietmar; Voit Brigitte; Gora-Tybor Joanna; Robak Tadeusz; Klaj: "Nanoparticles—a Novel Approach to Chronic Lymphocutic Leukemia Treatment?", Blood, vol. 120, No. 21, Nov. 16, 2012 (Nov. 16, 2012), p. 4601, XP055107869, 54th Annual Meeting and Exposition of American-Society-of-Hematology (ASH); Atlanta, GA, USA; Dec. 8-11, 2012 ISSN:0006-4971 abstract.

A. Janaszewska et al: "Cytotoxicity of Pamam, PPI and Maltose modified PPI dendrimers in Chinese hamster ovary (CHO) and human ovarian carcinoma (SKOV3) cells", New Journal of Chemistry, vol. 36, No. 2, Jan. 1, 2012 (Jan. 1, 2012), p. 428, XP055107809, ISSN: 1144-0546, DOI: 10.1039/c1nj20489k abstract.

Prashant Kesharwani et al: "Cancer targeting potential of some ligand-anchored poly(propylene imine) dendrimers: a comparison", Nanomedicine: Nanotechnology, Biology and Medicine, Elsevier, NL, vol. 7, No. 3, Oct. 27, 2010 (Oct. 10, 2010), pp. 295-304, XP028219877, ISSN: 1549-9634, DOI: 10.1016/J.NANO.2010.10.010 [retrieved on Nov. 9, 2010] abstract.

Barbara Ziemba et al: "Toxicity and proapoptotic activity of poly(propylene imine) glycodendrimers in vitro: Considering their contrary potenial as biocompatible entity and drug molecule in cancer", International Journal of Pharmaceutics, vol. 461, No. 1-2, Jan. 1, 2014 (Jan. 1, 2014), pp. 391-402, XP055107830, ISSN:0378-5173, DOI: 10.1016/j.ijpharm.2013.12.011 the whole document.

Fig. 1

Pattern of PPI-G4-OS-Mal-III dendrimer particle

The cytometric analysis of apoptotic CLL cells under the influence of PPI-G4-OS-Mal-III dendrimer.

Fig. 2

The cytometric analysis of apoptosis in healthy lymphocytes under the influence of PPI-G4-OS-Mal-III dendrimer

Fig. 3

APPLICATION OF MALTOTRIOSE-COATED 4TH GENERATION POLYPROPYLENEIMINE DENDRIMER PPI-G4-OS-MAL-III

Figure 1:
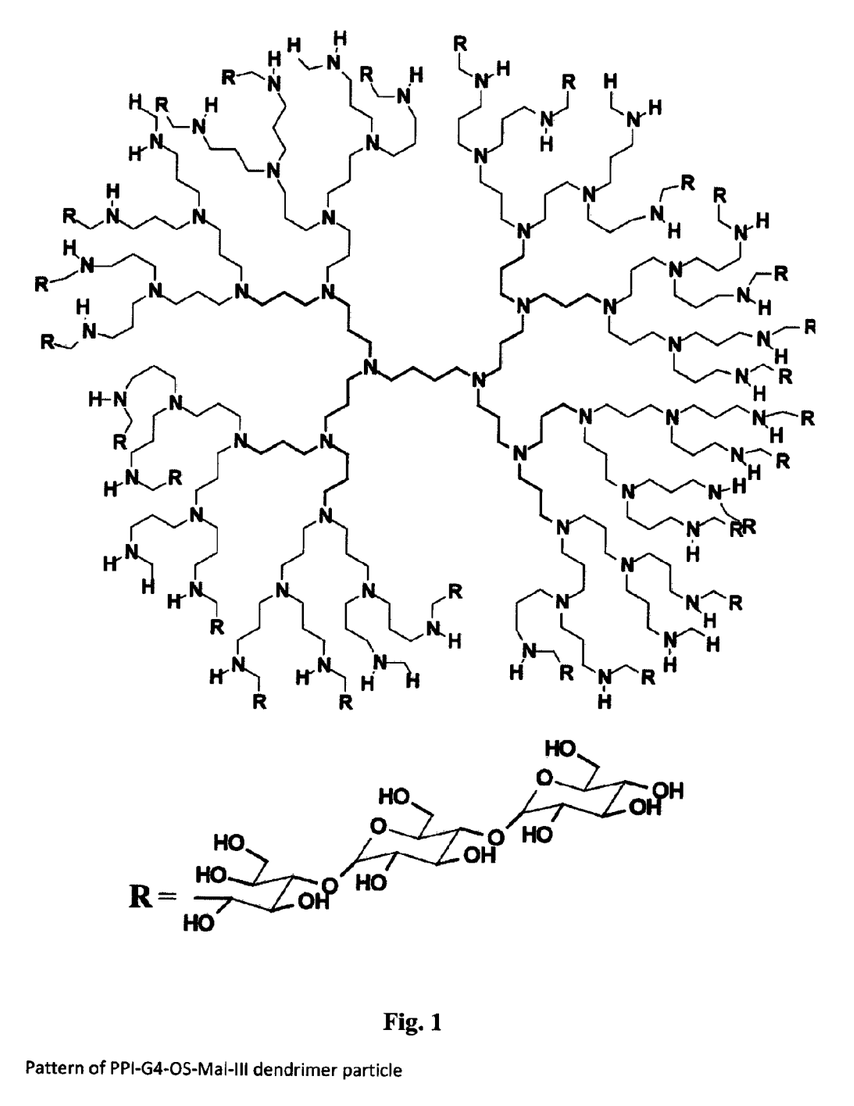

The invention is designed for the application of maltotriose-coated 4th generation polypropyleneimine dendrimer PPI-G4-OS-Mal-III, which is defined by pattern 1 with its R component standing for a maltotriose particle (trisaccharide made of 3α-glucose residues) and designated in short as PPI-G4-OS-Mal-III—where PPI-G4 stands for the 4th generation of polypropyleneimine dendrimer, OS (open Shell) for an open coat and Mal-III for maltotriose.

For a long time extensive research has been conducted to investigate into new effective drugs to treat hematomalignancies. For many years, standard treatment of chronic lymphocytic leukemia (CLL) was based on the application of alkylating drugs such as nitrogen mustard, cyclophosphamide or chlorambucyl being a drug of choice. In the 1980s, first compounds belonging to the so-called group of purine analogues (ANP) were synthesised. Two of them, i.e. cladribine (2-chlordeoxyadenosin; 2-CdA) and fludarabine (FA) are routinely used in CLL therapy, as well as in other myelo- and lymphoproliferative disorders. Recently, a few monoclonal antibodies and immunotoxins have been introduced into CLL treatment. Monoclonal antibodies, e.g. rituximab, administered in combination with ANP, increase the effectiveness of CLL therapy.

Despite all this wide range of antileukemic drugs, CLL is still an incurable disease. Therefore, an investigation into new therapeutics, which might fight off the disease, has a deep sense, and a breakthrough in effectiveness of its treatment is much expected.

In neoplastic diseases a proliferation mechanism, i.e. the organism's ability to proliferate cells, is, in case of neoplastic cells, unlimited and uncontrolled proliferation of injured cells, which results in the occurrence of neoplastic processes in the organism. In particular, leukemic lymphocytes are regarded as showing an intensified mechanism of proliferation resulting in the occurrence of an increased number of lymphocytes in the organism in relatively short time, which leads to accumulation of harmful B-lymphocytes in blood circulation (lymphocytosis) and a fast development of the neoplastic disease. A generally known fact (paradigm) in case of chronic lymphocytic leukemia (CLL) is the occurrence of a defect (injury) of the natural process of a programmed death of cells, i.e. apoptosis of leukemic lymphocytes present in a human organism.

An intensified worldwide development of neoplastic diseases makes us investigate into a new effective drug or drug component eliminating neoplastic diseases, including a chronic lymphocytic leukemia (CLL), a disease that is very dangerous to humans. Therefore, there is an urgent need to do research and investigate into a drug component/drug against CLL showing an ability to induce apoptosis in leukemic lymphocytes, inhibiting their proliferation (unlimited proliferation) and showing no toxicity towards other healthy blood cells at the same time.

In the 21st century, nanotechnology has been a field of studies developing rapidly. Therefore, investigations into substances that might be effective in the fight against neoplasm have been conducted in this particular area. Biologically applied nanoparticles, which have become known recently, are chemical polymeric compounds with a branched structure given the name of dendrimers. These are used as carriers of anticancer drugs through conjugation or encapsulation.

In the publication of Omidi Y, Hollins A J, Drayton R M, Akhtar S. J Drug Target (2005), 13: 431-443 polypropyleneimine dendrimers (PPI) of the second and third generation used for gene (DNA fragments of a known sequence) transfection (introduction into the cell) in oncogenic lines (causing lung and skin neoplasm) were revealed. Genes introduced into neoplastic cells subject to research changed endogenous gene expression (pre-existent in the cell), also in apoptosis-related genes. It had a very advantageous impact on therapeutic results (gene therapy) resulting in death of oncogenic cells. It has been also observed that PPI vector introduced in the neoplastic cell activated genes inducing a mechanism of apoptosis.

In the publication of M Mkandawire, A Pohl, T Gubarevich, V Lapina, D Appelhans, G Rödel, W Pompe, J Schreiber, J Opitz. Selective targeting of green fluorescent nanodiamond conjugates to mitochondria in HeLa cells. J Biophotonics. 2009; 2:596-606, the use of PPI-G4 dendrimers with their surface being partially maltotriose-modified (PPI-G4-OS-Mal-III) has been described in biomedical studies as carriers indicating great effectiveness in transfection of fluorescent biomarkers (nanodiamonds) towards HeLa cells.

In the studies of drugs application at particular disease stages an important criterion determining whether they are administered or not is their toxicity level for human cells. PPI-G4 polypropyleneimine dendrimers show very high toxicity. Thus, attempts are made to synthesize dendrimers of low toxicity as being useful in both biomedical studies and medical therapies.

Taking into account future development and availability of nanoparticles such as dendrimers, the Authors of this invention conducted extensive research with an intention to invent compounds of small molecular mass, which are capable of acting by inducing a mechanism of apoptosis in leukemic cells and showing, at the same time, low toxicity to other morphotic elements of blood.

The subject matter of the invention is the application of polypropyleneimine dendrimer of the fourth generation, coated with maltotriose, defined by the pattern 1 with its R component standing for a maltotriose particle and designated in short as PPI-G4-OS-Mal-III—where PPI-G4 stands for the 4th generation of polypropyleneimine dendrimer, OS (open shell)—open coat, Mal-III for maltotriose (trisaccharide made of 3α-glucose residues), to make a drug for treating proliferative neoplastic diseases, particularly chronic lymphocytic leukemia.

It is advantageous that PPI-G4-OS-Mal-III dendrimer contains 25-45%, more advantageously, 35% of maltotriose particles—Mal-III, related to amino groups of the 4th generation polypropyleneimine dendrimer particle PPI-G4, forming an open coat (open shell) of PPI-G4 dendrimer.

Such a polypropyleneimine dendrimer of the fourth generation, coated with maltotriose PPI-G4-OS-Mal-III, which has been used in the invention in order to make a drug for treating proliferative neoplastic diseases with an impaired mechanism of apoptosis, including chronic lymphocytic leukemia, shows surprising effectiveness as an active substance causing apoptosis, i.e. a death of leukemic B-lymphocytes. It is by triggering an apoptosis mechanism that B leukemic lymphocytes die, and are next removed from the organism as injured leukemic cells and thus a therapy using PPI-G4-OS-Mal-III dendrimer gives positive effect.

Furthermore, PPI-G4-OS-Mal-III dendrimer shows no toxicity in relation to other morphotic elements of blood, and reveals more effective biodistribution in blood.

The PPI-G4-OS-Mal-III polypropyleneimine dendrimer of the fourth generation, coated with maltotriose, which has been used in the invention, and which contains maltotriose particles (Mal-III) in the dendrimer outer structure, was revealed in the publication by Appelhans D, Oertel U, Mazzeo R et al., Proc R Soc A 2010; 466:1489-1513, containing a description of its synthesis and properties, while in the Chem Eur J (2008), 14: 7030-7041 Klajnert B, Appelhans D, Komber H et al. described PPI-O4-OS-Mal-III dendrimer molar mass (MM) determined by magnetic resonance with use of $^1$HNMR spectrometric method, where the reading for atoms of hydrogen ($^1$H) was made at 500.13 MHz frequency. As shown in FIG. 1 and Table 1, surface amino groups of PPI-G4 dendrimer were maltotriose-saturated (Mal-III) in the range of approximately (22)—35% to form a dense dendrimer coat designated as OS (OS—with an open shell). Coating of dendrimers with maltotriose is conducted in Germany, in Leibnitz Institute of Polymer Research, Dresden. The product is not commercially available. However, the 4$^{th}$ generation PPI dendrimers (PPI-G4) are commercially available from Symo-Chem, Eindhoven, the Netherlands.

TABLE 1

Molar mass (MM$^a$) of commercially available PPI-G4 and synthesized PPI-G4-OS-Mal-III; the number and the percentage of surface maltotriose groups.

| Dendrimer | MM$_{theoretical}$ (g/mol) | MM$_{observed}$ (g/mol) | Number (percentage) of surface Mal-III groups$_{theoretical}$ | Number (percentage) of surface Mal-III groups$_{observed}$ |
|---|---|---|---|---|
| PPI-G4 | 3514 | 3514 | — | — |
| PPI-G4-OS-Mal-III | 19144 | 14260 | 32 (50%) | 22 (35%) |

PPI-G4-OS-Mal-III dendrimer used in this invention was subject to tests of the IC$_{50}$, a toxicity indicator, which was defined as the concentration of dendrimers that caused 50% cytotoxicity of cytotoxicity of leukemic lymphocytes (MNCs). The IC$_{50}$ for PPI-G4-OS-Mal-III dendrimer used alone was 8.24 mg/ml in 48-hour cultures. Calculation of the IC$_{50}$ allows to adjust the dose of PPI-G4-OS-Mal-III dendrimer in the drug for the needs of antineoplastic therapy in treating proliferative neoplastic disorders with a disturbed apoptosis mechanism, which is the case in chronic lymphocytic leukemia, and to make the drug in various pharmaceutical forms according to generally known methods.

This invention shall be described in the examples below. The subject matter of the invention has been illustrated in the figure, in which:

FIG. 1—presents a particle of maltotriose modified 4th generation polypropyleneimine dendrimer described in short as PPI-G4-OS-Mal-III, FIG. 2—presents a two-variant 'dot-plot' type histogram of control leukemic B lymphocytes, which were not treated with dendrimer, and leukemic B lymphocytes, which were treated with PPI-G4-OS-Mal-III dendrimer, and tested. In the double staining method applied (propidium iodide and annexin-V) to leukemic lymphocytes in CLL, one may observe cells being at various stages of programmed cell death (early apoptosis, late apoptosis, necrosis), FIG. 3—presents a two-variant 'dot-plot' type histogram of healthy control B-lymphocytes, which were not treated with dendrimer, and healthy B lymphocytes, which were treated with PPI-G4-OS-Mal-III dendrimer, and tested. In the double staining method applied (propidium iodide and annexin-V) to leukemic lymphocytes in CLL, one may observe cells being at various stages of programmed cell death (early apoptosis, late apoptosis, necrosis), and test results from the examples presented were given in tables, where Table 2—presents results of mean percentage of leukemic lymphocytes in in vitro cultures subject to apoptosis or necrosis under the influence of PPI-G4-OS-Mal-III dendrimer in four concentrations examined; in addition, the results provide for the values of standard deviation in relation to each mean value and statistical analysis, Table 3—presents results of mean percentage of healthy lymphocytes in in vitro cultures subject to apoptosis or necrosis under the influence of PPI-G4-OS-Mal-III dendrimer in four concentrations examined; in addition, the results provide for the values of standard deviation in relation to each mean value and statistical analysis, Table 4—presents results of averaged percentage of cells—leukemic lymphocytes with a decreased mitochondrial potential in in vitro cultures under the influence of PPI-G4-OS-Mal-III dendrimer in three concentrations examined and under the influence of two drugs most frequently used in CLL therapy, i.e. fludarabine (purine analogue) and rituximab (monoclonal antibody).

EXAMPLE 1

An ability to induce the apoptosis process in leukemic lymphocytes using 4th generation polypropyleneimine dendrimer coated with maltotriose PPI-G4-OS-Mal-III containing 35% of maltotriose and cytotoxicity of this dendrimer in the foregoing cells were studied—in vitro studies a) Isolation and Culture of MNCs Mononuclear Cells (Leukemic Lymphocytes) in Vitro The research material was peripheral blood collected from 15 patients, who had not been earlier treated for chronic lymphocytic leukemia (CLL) (8 women (K) and 7 men (M) at the age of 39-85 (mean age was 63.8), and who were registered as patients of the Hematology Outpatient Clinic and Hematology Department, Medical University, Łódź, Poland. The Ethics Committee of the Medical University of Łódź, Poland approved the study (RNN/75/10/KE). Informed consent was obtained from all patients involved in the study.

Mononuclear cells (MNCs), of which a majority (approx. 90%) were B leukemic lymphocytes, were isolated from peripheral blood collected onto disodium versenate—EDTA as an anticoagulant. Next, blood was layered onto Histopaque 1077 (Sigma, St. Louis, USA) in the test tube and centrifuged on a density gradient for 20 minutes at 200 g acceleration (where 'g' means gravity acceleration). A ring of MNCs obtained at the phase boundary was isolated and washed twice with RPMI-1640 medium (PAA, Germany). MNCs obtained were suspended in RPMI-1640 medium at the concentration of $1\times10^6$ cells/ml; the following was subsequently added: 20% of inactivated foetal bovine serum (FBS) and antibiotics such as streptomycin, gentamicin (5 ml mixture of antibiotics per 500 ml culture medium), (PAA, Germany) and PPI-G4-OS-Mal-III dendrimer containing 35% of maltotriose in a given concentration tested (concentrations are listed below). The cultures were made in the final volume of 1 ml in the RPMI-1640 medium. The culture of MNCs was incubated in a biological incubator for 24 hours with an inflow of 5% CO$_2$ at 37° C., 98% humidity. Following the incubation process, a qualitative and quantitative assessment of MNCs apoptosis and cytotoxicity was carried out.

Using the foregoing assay, cultures of lymphocytes MNCs were made to perform tests with PPI-G4-OS-Mal-III dendrimer containing 35% in the following volumes:
- 4 mg/ml of culture medium,
- 6 mg/ml of culture medium,
- 8 mg/ml of culture medium,
- 10 mg/ml of culture medium.

In addition, tests for cultures of lymphocyte MNCs were made for 48-hours-incubation time.

The cultures made in the same conditions without PPI-G4-OS-Mal-III dendrimer containing 35% of maltotriose were considered as controls.

b) Assessment of Apoptosis and Cytotoxicity—Annexin-V and Propidium Iodide Tests Following incubation, MNCs leukemic lymphocytes were washed twice in cool buffered saline solution (PBS—saline water solution containing sodium chlorine and sodium phosphate), and next the cells were suspended in a binding buffer containing 5 µl FITC (fluorescein isothiocyanate dye) conjugated with annexin-V (Ann-V) and 10 µg/ml of propidium iodide (IP). The samples were next incubated for 15 minutes in darkness at room temperature, and their fluorescence was immediately assessed using a flow cytometer (FACSCalibur Becton Dickinson), wavelength being FL1 490"±20 nm and FL3 530"±20 nm.

Propidium iodide (IP) is cationic solution showing autofluorescence, which is actively eliminated by healthy cells, while the cell membrane integrity is maintained (IP cells—negative, IP−). Annexin-V changes the cell membrane integrity causing a displacement of phosphatidylserine to the cell membrane outer monolayer. Cytotoxicity of the compound is demonstrated through disorders of IP release to the environment (IP-positive cells, IP+).

In order to calculate an apoptic index (AI) the cells stained with Annexin-V (AnnV+IP− and AnnV+/IP+) were assessed. Cytotoxicity of PPI-G4-OS-Mal-III containing 35% of maltotriose dendrimers was estimated by measuring viability of leukemic lymphocytes MNCs stained with IP.

c) Assessment of Mitochondrial Membrane Potential (Early Marker of Apoptosis)

Mitochondrial membrane potential is an early indicator of apoptosis. CMXRos, i.e. Chloromethyl-X-rosamine (the reagent's name by Mito Tracker Red CMXRos, Molecular Probes, USA), and a monoclonal antibody to glycophorin A conjugated with FITC (the reagent's name of Anti-Glycophorin A FITC by Dako, Denmark) were used for its assessment. CMXRos is a lipophilic cationic dye that accumulates in the mitochondrial matrix of viable cells when there is an electronegative load on the inner surface of the mitochondrial membrane. This asymmetric location of protons along the inner mitochondrial membrane leads to a high mitochondrial membrane potential ($\Delta\Psi m$) in living cells. A decreased $\Delta\Psi m$ is one of the first symptoms of apoptosis, and in effect lowering of the mitochondrial uptake of CMXRos.

The stock CMXRos solution was prepared by dilution of the substance supplied by the manufacturer in 94 µl DMSO (dimethylsulphoxide), and stored at 20° C. Then working solution was prepared also using DMSO (1:10) and stored at 4° C. Mononuclear cells, i.e. leukemic lymphocytes, at $1\times10^6$ MNCs/ml concentration, were incubated with CMXRos (2.5 µl working solution in 500 µl RPMI 1640 medium) at 37° C. for 30 minutes. Exactly after 15 minutes, 5 µl of monoclonal antibody against glycophorin A conjugated with FITC was added to eliminate any incidental erythrocytes in the sample, which might give a wrong positive result due to low mitochondrial potential. The samples were next measured using flow cytometry. The percentage of cells not bound to anti-glycophorin A-FITC ($\Delta\Psi m^{low}$/Gly-A− cells), with low mitochondrial potential, was calculated.

All fluorescence measurements were performed by a flow cytometer FACSCalibur (Becton Dickinson, USA) equipped with argon laser 488 nm and computer program CellQuest-Pro (Becton Dickinson, USA). Each time 10 000 events were evaluated. The fluorescence was measured using standard emission filters: green—FL1 (wavelength $\lambda=530\pm20$ nm) and red—FL3 (>600 nm).

d) Statistical Analysis

Significant statistical differences between the results obtained in cultures of leukemic lymphocytes (MNCs), where PPI-G4-OS-Mal-III dendrimer containing 35% of maltotriose was added as in the invention and control cultures, where no such PPI-G4-OS-Mal-III dendrimer was added, were compared using Wilcoxon rank test and assuming that statistically significant differences were those in which a significance level was $p<0.05$.

The $IC_{50}$ toxicity indicator of PPI-G4-OS-Mal-III dendrimer was defined as the concentration of dendrimers that caused 50% cytotoxicity of leukemic lymphocytes (MNCs). Calculation of the $IC_{50}$ allows adjusting the dose of the drug containing PPI-G4-OS-Mal-III dendrimer for the needs of antineoplastic therapy. If it is necessary for a single dose of the drug to be so toxic as to destroy 100% cells against which it is directed, then in such a drug dose the PPI-G4-OS-Mal-III dendrimer concentration is twice as high as the concentration causing death of 50% of leukemic cells. This applies to drug doses for patients with progressive disease in whom a fast therapeutic effect would be recommended (fewer tablets given in short time). In case of weaker patients, e.g. elderly patients, a dose of the drug containing PPI-G4-OS-Mal-III dendrimer shall be established at the concentration reduced by half to destroy leukemic lymphocytes. The therapy shall take more time, and there will be fewer adverse effects as a response to the cell disintegration process; however, the final therapeutic effect shall be achieved (more tablets taken in longer time by the patient, therapeutic effect achieved).

e) Results Received

Figure 2:
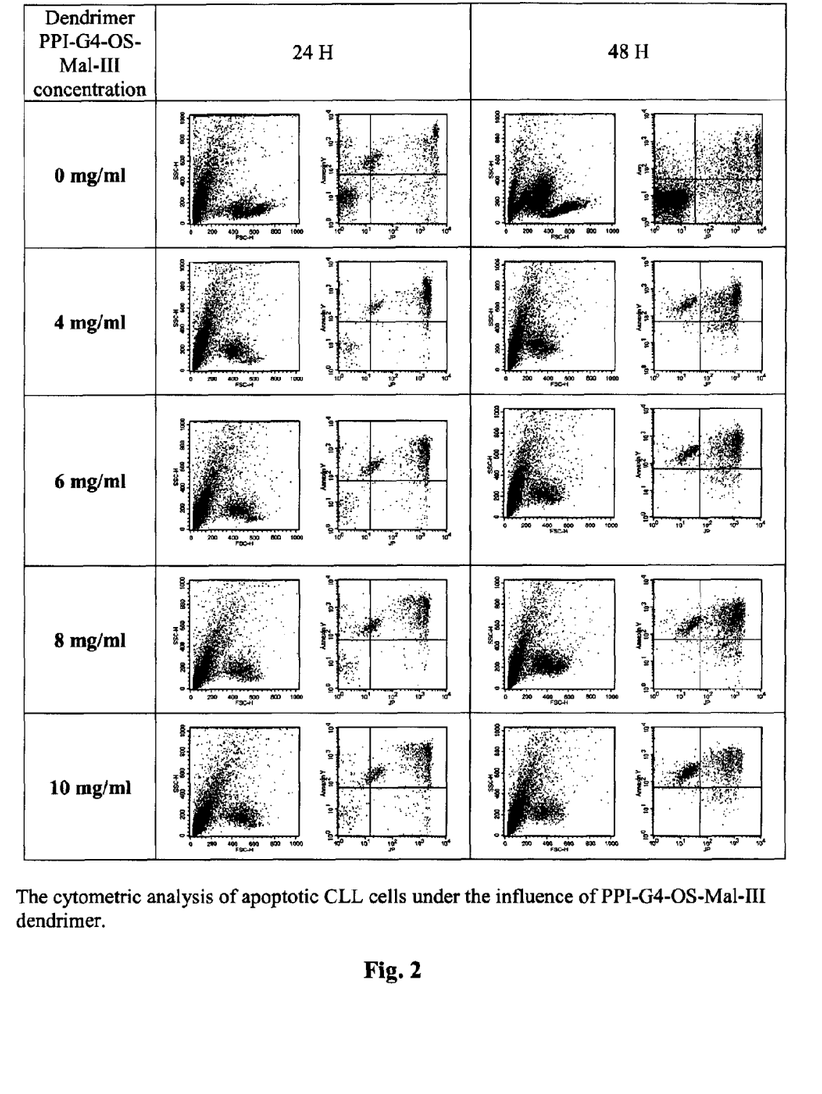

The percentage of apoptotic MNCs induced by PPI-G4-OS-Mal-III dendrimer in each concentration after 24 h and 48 h incubations was significantly higher than the percentage of spontaneous apoptotic leukemic cells ($p<0.05$) (Table 2). Cytometric analysis of CLL cells undergoing apoptosis is shown in FIG. 2. A higher percentage of cells undergoing apoptosis was observed for 48 h incubation time, compared to 24 h. The greatest differences for late apoptotic cells (Ann-V$^+$IP$^+$) were shown after 48 h incubation at two dendrimer concentrations of 8 mg/ml ($p=0.007$) and 10 mg/ml ($p=0.007$), however, after 24 h incubation the difference from controls was also significant ($p=0.005$) (Table 2).

PPI-G4-OS-Mal-III dendrimer did not markedly induce an early apoptosis (Ann-V$^+$IP$^-$) of CLL cells. No statistically significant differences were observed for the percentage of CLL necrotic cells as compared to control cultures either in 24 h-cultures or in 48 h-cultures. This indicates that the tested dendrimer PPI-G4-OS-Mal-III causes CLL cells' death by inducing the apoptosis mechanism and does not act directly on the cell membrane by interrupting its integrity. $IC_{50}$ for PPI-G4-OS-Mal-III dendrimer used alone was 8.24 mg/ml.

Another method confirming the activity of PPI-G4-OS-Mal-III dendrimer via the mechanism of apoptosis on CLL cells is the evaluation of mitochondrial potential. In 24-hour cultures with dendrimer in three concentrations, i.e. 4 mg/ml, 6 mg/ml, 8 mg/ml, the number of apoptotic cells was significantly higher than the number of cells in the control culture. The percentage of apoptotic cells increased proportionally with increasing concentrations of the dendrimer. The apoptotic cells rate after the incubation with the purine analogue (FA, fludarabine) at the concentration of 1.6 µM was comparable to the percentage of apoptotic cells for the PPI-G4-OS-Mal-III dendrimer concentration of 6 mg/ml. Monoclonal antibody anty-CD20 (Rit, rituximab) at the concentration of 10 µg/ml showed apoptosis-inducing action in order of spontaneous apoptosis (in control samples). After 48 h in cell cultures with the dendrimer, the percentage of cells $\Delta\Psi m^{low}$/Gly-A$^-$ was significantly higher (68.57-78.56%) than the percentage of cells in the control culture (42.04%). The results are shown in Table 4.

EXAMPLE 2

An ability to induce the apoptosis process in healthy blood cells using 4th generation polypropyleneimine dendrimer coated with maltotriose PPI-G4-OS-Mal-III containing 35% of maltotriose, and cytotoxicity of this dendrimer in the foregoing cells were studied—in vitro studies a) Assessment of the Apoptosis Induction and PPI-G4-OS-Mal-III Dendrimer's Cytotoxicity in MNCs from Healthy Volunteers The research material was peripheral blood collected from 5 healthy volunteers, (3 women and 2 men) at the age of 25-65 (mean age was 38.00±10.80). Isolation of mononuclear cells (MNCs), cell cultures, also assessment of apoptosis and cytotoxicity were made using the same method as in Example 1.

Figure 3:
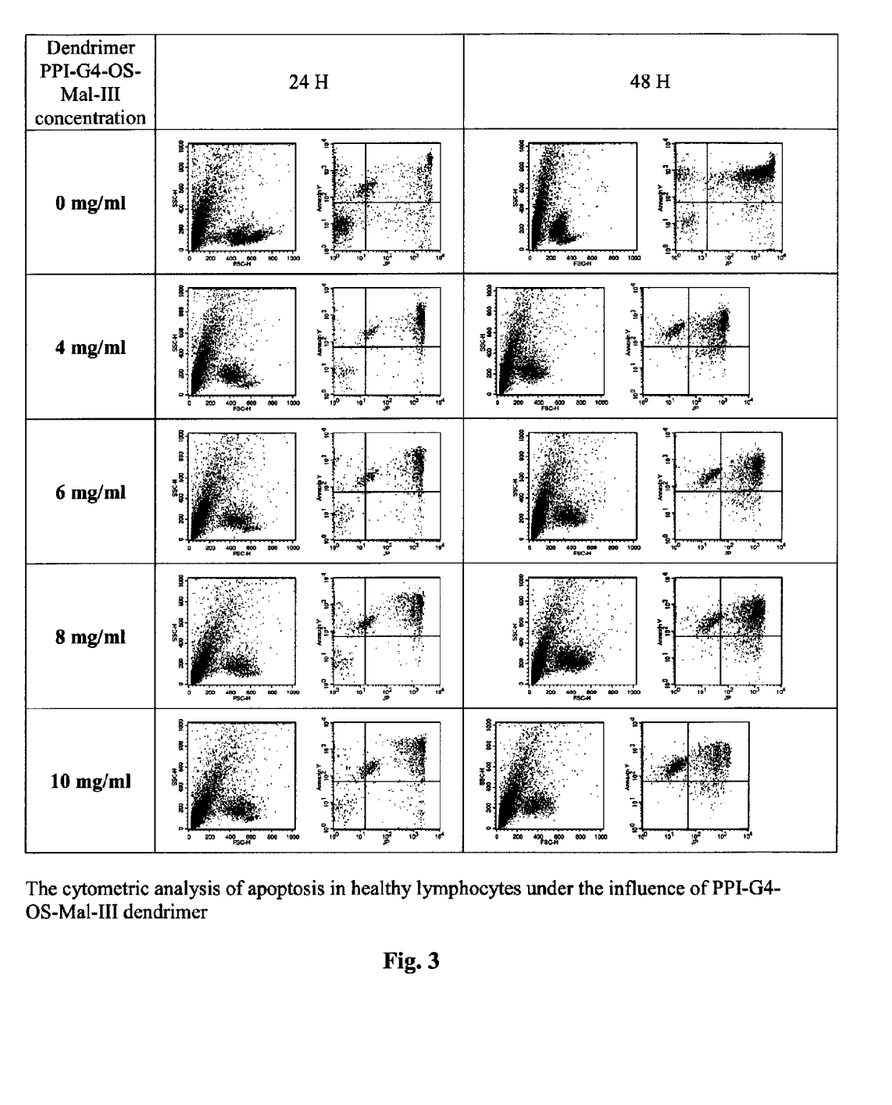

The effect of PPI-G4-OS-Mal-III dendrimer on healthy mononuclear cells is negligible; however, differences between control cultures and cultures with dendrimer show statistical significance. It is only after 48 h that higher percentage of apoptotic cells was observed for higher dendrimer concentrations. Statistically significant results were obtained for late apoptosis at every examined dendrimer PPI-G4-OS-Mal-III concentration (p=0.03). The percentage of dead cells IP stained after 24 h incubation was approximately 23.33% to 25.33% for PPI-G4-OS-Mal-III dendrimer concentration of 8 mg/ml, whereas it was 12.38% for the dendrimer untreated cells. As demonstrated by the presented results, PPI-G4-OS-Mal-III dendrimers show not much toxicity to healthy lymphocytes (Table 3, FIG. 3).

b) Influence of PPI-G4-OS-Mal-III Dendrimer on Inhibition or Induction of MNCs Lymphocytes Proliferation MNCs were isolated using the method of density gradient (as described in Example 1) from the blood of healthy volunteers. To assess the inhibition or induction of lymphocyte proliferation by PPI-G4-OS-Mal-III dendrimer, cells were incubated with or without the dendrimer, and either in the presence or absence of phytohemaglutinin (PHA-M) depending on whether it was a tested sample or a control one, respectively. After 72 h incubation, the samples were analysed spectrophotometrically by means of MTT (3-(4,5-dimethyl-2-thiazolyl)-2,5-diphenyl-2H-tetrazolium bromide). The final concentration of PHA-M was 10 µl/ml and PPI-G4-OS-Mal-III dendrimers were used at concentrations of 0.2; 0.04 and 0.008 mg/ml. The MNCs suspension with PHA-M solution at 10 µl/ml concentration in the culture medium was regarded as a positive—proliferating control, and the MNCs suspension in the PBS buffer was regarded as the negative-nonproliferating control.

The PPI-G4-OS-Mal-III dendrimer slightly restrained cell proliferation of healthy lymphocytes. This effect is of no considerable significance from the biological point of view. The ability to inhibit proliferation increases proportionally with increasing concentration of the dendrimer PPI-G4-OS-Mal-III.

c) Influence of PPI-G4-OS-Mal-III Dendrimer on Erythrocyte Haemolysis

In the samples subject to tests the level of haemolysis was determined on the basis of haemoglobin (HGB) released into the supernatant during centrifuging of 1000 g for 5 minutes, and after prior incubation at 37° C. for 2, 4, 16 and 24 h. For reference (100% haemolysis), erythrocytes were treated with distilled water. The PPI-G4-OS-Mal-III dendrimers did not cause erythrocyte haemolysis in contrast to unmodified dendrimers (PPI-G4). It is obvious from the above observation that PPI-G4-OS-Mal-III dendrimer containing 35% of maltotriose is safe for erythrocytes; it does not destroy their cell membranes.

d) Influence of PPI-G4-OS-Mal-III Dendrimers on Platelets (PLT) Aggregation

Blood from healthy donors was collected onto CPDA-1 anticoagulant (100 mM glucose; 55 mM mannitol; 25.8 mM $K_2HPO_4$; 14.7 mM $KH_2PO_4$; 17.9 mM potassium citrate); (mM—molar mass). Blood plasma was centrifuged at 360 g (g—gravity acceleration) for 5 minutes. PLTs pellet (a cluster of cells following centrifuging devoid of supernatant) was suspended in Tris (TRIS—tris(hydroxymethyl)aminomethane) buffer containing EDTA (0.12 M NaCl, 0.0154 M KCl, 0.006 glucose, 0.0015 M $Na_2EDTA$, 0.0133 M Tris; pH 6.5) (M—mol). The suspension was centrifuged at 360 g for 5 minutes. The PLTs pellet was re-suspended in the buffer at concentration of $2.0 \times 10^9$ cells/ml (TRIS buffer). Aggregation of PLTs was determined using an automatic agregometer AP2110. Trypsin at concentration of 1 µg/ml was added to PLTs as a positive control.

The PPI-G4-OS-Mal-III dendrimer caused the PLT aggregation in 20% at the concentration of 10 mg/ml and higher.

As described above, PPI-G4-OS-Mal-III dendrimer supplementation to CLL lymphocytes significantly induces the mechanism of apoptosis in these cells, thus considerably reducing their proliferation and survival. It has been proved that one may expect an effective therapeutic effect in treating proliferative neoplastic diseases, particularly chronic lymphocytic leukemia (CLL), using the PPI-G4-OS-Mal-III dendrimer as a drug. At the same time, it has been proved that the PPI-G4-OS-Mal-III dendrimer applied in the way presented in the invention, is non-toxic to other morphotic elements of blood (erythrocytes, platelets), which ensures its safe use in humans.

page 15—Table 2
page 16—Table 3
page 17—Table 4

TABLE 2

The influence of PPI-G4-OS-Mal-III dendrimers on the apoptosis and viability of CLL cells in in vitro cultures.

|  | Control | | | PPI-g4-OS-Mal-III 4 mg/ml | | | PPI-g4-OS-Mal-III 6 mg/ml | | |
| --- | --- | --- | --- | --- | --- | --- | --- | --- | --- |
|  | 1 | 2 | 3 | 4 | 5 | 6 | 7 | 8 | 9 |
| 24 h | | | | | | | | | |
|  | Ann + JP− | Ann + JP+ | Ann − JP+ | Ann + JP− | Ann + JP+ | Ann − JP+ | Ann + JP− | Ann + JP+ | Ann − JP+ |
| n | 15 | 15 | 15 | 15 | 15 | 15 | 15 | 15 | 15 |
| X | 9.46 | 7.57 | 4.25 | 11.84 | 22.41 | 6.94 | 14.46 | 22.79 | 5.82 |
| SD | 9.83 | 6.72 | 2.63 | 8.02 | 20.22 | 8.52 | 12.31 | 17.68 | 5.47 |
| 48 h | | | | | | | | | |
| n | 15 | 15 | 15 | 15 | 15 | 15 | 15 | 15 | 15 |
| X | 11.70 | 15.30 | 11.95 | 11.41 | 28.86 | 8.80 | 10.23 | 31.07 | 8.61 |
| SD | 8.75 | 11.77 | 13.61 | 9.84 | 20.42 | 5.52 | 7.91 | 21.78 | 6.09 |

|  | PPI-g4-OS-Mal-III 8 mg/ml | | | PPI-g4-OS-Mal-III 10 mg/ml | | | Statistical analysis (p) |
| --- | --- | --- | --- | --- | --- | --- | --- |
|  | 10 | 11 | 12 | 13 | 14 | 15 | 13 |
| 24 h | | | | | | | |
|  | Ann + JP− | Ann + JP+ | Ann − JP+ | Ann + JP− | Ann + JP+ | Ann − JP+ | 2 v 5 = 0.005 |
| n | 15 | 15 | 15 | 15 | 15 | 15 | 2 v 8 = 0.005 |
| X | 14.95 | 24.43 | 5.37 | 21.14 | 25.27 | 10.34 | 2 v 11 = 0.005 |
| SD | 12.71 | 18.14 | 5.58 | 22.14 | 26.93 | 5.23 | 2 v 14 = 0.005 |
| 48 h | | | | | | | |
| n | 15 | 15 | 15 | 15 | 15 | 15 | 2 v 5 = 0.05 |
| X | 10.25 | 34.76 | 12.46 | 15.47 | 45.66 | 15.02 | 2 v 8 = 0.01 |
| SD | 7.80 | 21.78 | 12.90 | 13.96 | 3.92 | 7.85 | 2 v 11 = 0.007 |
|  |  |  |  |  |  |  | 2 v 14 = 0.007 | n—number of samples;
X—mean percentage of apoptotic or necrotic cells;
SD—standard deviation;
Early apoptosis—$Ann^+IP^-$;
late apoptosis—$Ann^+IP^+$;
necrosis—$Ann^-IP^+$;
Ann—annexin-V;
IP—propidium iodide

TABLE 3

The influence of PPI-G4-OS-Mal-III dendrimers on the apoptosis and viability of healthy cells in in vitro cultures.

|  | Control | | | PPI-g4-OS-Mal-III 4 mg/ml | | | PPI-g4-OS-Mal-III 6 mg/ml | | |
| --- | --- | --- | --- | --- | --- | --- | --- | --- | --- |
|  | 1 | 2 | 3 | 4 | 5 | 6 | 7 | 8 | 9 |
| 24 h | | | | | | | | | |
|  | Ann + JP− | Ann + JP+ | Ann − JP+ | Ann + JP− | Ann + JP+ | Ann − JP+ | Ann + JP− | Ann + JP+ | Ann − JP+ |
| n | 5 | 5 | 5 | 5 | 5 | 5 | 5 | 5 | 5 |
| X | 11.00 | 4.11 | 8.27 | 6.68 | 15.53 | 7.11 | 7.53 | 17.15 | 8.61 |
| SD | 1.97 | 0.76 | 1.22 | 1.91 | 2.46 | 1.29 | 2.39 | 3.10 | 2.40 |
| 48 h | | | | | | | | | |
| n | 5 | 5 | 5 | 5 | 5 | 5 | 5 | 5 | 5 |
| X | 18.05 | 13.02 | 10.56 | 7.91 | 23.90 | 7.96 | 7.19 | 25.45 | 12.63 |
| SD | 4.71 | 1.22 | 3.41 | 1.49 | 5.27 | 1.43 | 1.87 | 5.42 | 3.56 |

TABLE 3-continued

The influence of PPI-G4-OS-Mal-III dendrimers on the apoptosis and viability of healthy cells in in vitro cultures.

| | | PPI-g4-OS-Mal-III 8 mg/ml | | | PPI-g4-OS-Mal-III 10 mg/ml | | Statistical analysis (p) |
|---|---|---|---|---|---|---|---|
| | 10 | 11 | 12 | 13 | 14 | 15 | 13 |
| | | | | 24 h | | | |
| | Ann + JP− | Ann + JP+ | Ann − JP+ | Ann + JP− | Ann + JP+ | Ann − JP+ | 1 v 4 = 0.04 |
| n | 5 | 5 | 5 | 5 | 5 | 5 | 2 v 5 = 0.04 |
| X | 8.55 | 16.53 | 8.80 | 10.66 | 19.75 | 11.66 | 2 v 8 = 0.04 |
| SD | 2.84 | 3.23 | 1.82 | 2.35 | 1.57 | 3.13 | 2 v 11 = 0.04 |
| | | | | | | | 2 v 14 = 0.04 |
| | | | | 48 h | | | |
| n | 5 | 5 | 5 | 5 | 5 | 5 | 2 v 5 = 0.03 |
| X | 8.70 | 26.17 | 10.09 | 9.39 | 32.10 | 9.54 | 2 v 8 = 0.03 |
| SD | 2.26 | 6.43 | 1.54 | 3.23 | 5.79 | 1.40 | 2 v 11 = 0.03 |
| | | | | | | | 2 v 14 = 0.03 | n—number of samples;
X—mean percentage of apoptotic or necrotic cells;
SD—standard deviation;
Early apoptosis—Ann⁺IP⁻;
late apoptosis—Ann⁺IP⁺;
necrosis—Ann⁻IP⁺;
Ann—annexin-V;
IP—propidium iodide

TABLE 4

The influence of PPI-G4-OS-Mal-III dendrimers on CLL cell mitochondrial potential in cultures in vitro. The comparison with purine analogue (fludarabine; FA) and monoclonal antibody (rituximab; Rit).

| | Control | PPI-G4-OS-Mal-III 4 mg/ml | PPI-G4-OS-Mal-III 6 mg/ml | PPI-G4-OS-Mal-III 8 mg/ml | FA 1.6 μM | Rit 10 μg/ml |
|---|---|---|---|---|---|---|
| | | | | 24 h | | |
| n | 10 | 10 | 10 | 10 | 10 | 10 |
| X | 37.91 | 49.30 | 59.88 | 63.98 | 52.05 | 44.92 |
| SD | 16.23 | 12.94 | 15.12 | 13.49 | 17.81 | 16.70 |
| | | | | 48 h | | |
| n | 10 | 10 | 10 | 10 | 10 | 10 |
| X | 42.04 | 68.57 | 70.88 | 78.56 | 74.49 | 60.58 |
| SD | 14.26 | 18.49 | 15.45 | 11.56 | 17.47 | 19.99 | n—numer of samples;
X—mean percentage of cells with lower mitochondrial potential ($\Delta\Psi m^{low}$/Gly-A⁻ [%]);
SD—standard deviation;
FA—fludarabine;
Rit—rituximab

The invention claimed is:

1. A method of administering a therapeutically effective amount of a maltotriose-coated 4th generation polypropyleneimine dendrimer—PPI-G4-OS-Mal-Ill of FIG. 1, where R stands for a maltotriose residue, to a human subject, comprising the steps:
   a) preparing the maltotriose-coated 4th generation polypropylene imine dendrimer—PPI-G4-OS-Mal-III of FIG. 1, where R stands for a maltotriose residue, in form suitable for i.v. administration, comprising a vehicle or diluent and optionally other suitable biologically active substances, and b) administering intravenously the maltotriose-coated 4th generation polypropyleneimine dendrimer—PPI-G4-OS-Mal-III of FIG. 1, wherein R stands for a maltotriose residue.

2. The method according to claim 1 for treating or alleviating a blood neoplastic proliferative diseases with an impaired mechanism of apoptosis of a human in need thereof, said method consisting of i.v. administration of a therapeutically effective amount of a maltotriose-coated 4th generation polypropyleneimine dendrimer—PPI-G4-OS-Mal-III of FIG. 1 where R stands for a maltotriose residue, wherein said maltotriose-coated 4th generation polypropyleneimine dendrimer—PPI-G4-OS-Mal-III is administered intravenously.

3. The method according to claim 2, wherein the blood neoplastic proliferative disease with an impaired mechanism of apoptosis is a chronic lymphocytic leukemia in humans.

4. The method according to claim 2, wherein the therapeutically effective amount of said PPI-G4-OS-Mal-III dendrimer is administered together with a physiological saline buffer, such as PBS (phosphate-buffered saline) as a pharmaceutically acceptable solvent suitable for i.v. administration.

5. The method according to claim 4, wherein the pharmaceutically acceptable solvent suitable for i.v. administration further comprises other adjuvants and/or biologically active substances.

* * * * *